(12) United States Patent
Jeanne et al.

(10) Patent No.: US 10,271,746 B2
(45) Date of Patent: Apr. 30, 2019

(54) METHOD AND SYSTEM FOR CARRYING OUT PHOTOPLETHYSMOGRAPHY

(75) Inventors: Vincent Jeanne, Eindhoven (NL); Giovanni Cennini, Eindhoven (NL); Ihor Olehovych Kirenko, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 13/500,336

(22) PCT Filed: Oct. 4, 2010

(86) PCT No.: PCT/IB2010/054462
§ 371 (c)(1),
(2), (4) Date: Apr. 5, 2012

(87) PCT Pub. No.: WO2011/042851
PCT Pub. Date: Apr. 14, 2011

(65) Prior Publication Data
US 2012/0197137 A1    Aug. 2, 2012

(30) Foreign Application Priority Data
Oct. 6, 2009 (EP) .................................. 09172345

(51) Int. Cl.
*A61B 5/00* (2006.01)
*A61B 5/02* (2006.01)
(Continued)

(52) U.S. Cl.
CPC ........ *A61B 5/0261* (2013.01); *A61B 5/02028* (2013.01); *A61B 5/02416* (2013.01); *A61B 5/1455* (2013.01); *A61B 5/7214* (2013.01)

(58) Field of Classification Search
CPC ............ A61B 5/02028; A61B 5/02416; A61B 5/0059; A61B 5/14552; A61B 1/042;
(Continued)

(56) References Cited

U.S. PATENT DOCUMENTS 4,958,638 A    9/1990  Sharpe et al.
5,299,570 A *  4/1994  Hatschek .................... 600/479
(Continued)

FOREIGN PATENT DOCUMENTS

CN    1946336 A      4/2007
CN    101309634 A    11/2008
(Continued)

OTHER PUBLICATIONS

Yang, Boo-Ho et al. Development of the ring sensor for healthcare automation. Robotics and Autonomous Systems 30 (2000) 273-281.*
(Continued)

*Primary Examiner* — Jennifer Dieterle
*Assistant Examiner* — Helene Bor
(74) *Attorney, Agent, or Firm* — Larry Liberchuk (57) ABSTRACT

A method of photoplethysmography includes processing a signal based on at least one signal from at least one sensor arranged to capture light from a living subject to extract information on a characteristic of a periodic biological phenomenon. At least one of the signals from at least one sensor is obtained via sensing radiation as to a peak in an absorption spectrum of water.

20 Claims, 5 Drawing Sheets

(51) Int. Cl.
  *A61B 5/024* (2006.01)
  *A61B 5/026* (2006.01)
  *A61B 5/1455* (2006.01)

(58) Field of Classification Search
  CPC ....... A61B 5/0261; A61B 5/1455; A61B 5/72;
       A61B 5/7203; A61B 5/7207; A61B
       5/7214
  USPC .................. 600/300, 322, 476, 425; 128/653
  See application file for complete search history.

(56) References Cited

U.S. PATENT DOCUMENTS

| | | | |
|---|---|---|---|
| 5,582,168 A * | 12/1996 | Samuels et al. | 600/407 |
| 5,699,797 A * | 12/1997 | Godik | A61B 5/0261 600/407 |
| 5,995,856 A | 11/1999 | Mannheimer et al. | |
| 6,915,154 B1 | 7/2005 | Docherty | |
| 7,171,251 B2 | 1/2007 | Sarussi | |
| 7,507,203 B2 | 3/2009 | Sebastian et al. | |
| 7,738,935 B1 * | 6/2010 | Turcott | 600/336 |
| 7,904,139 B2 * | 3/2011 | Chance | 600/476 |
| 8,315,684 B2 * | 11/2012 | Petersen et al. | 600/336 |
| 9,668,661 B2 | 6/2017 | Melker | |
| 2002/0055672 A1 | 5/2002 | Zhang | |
| 2008/0045847 A1 | 2/2008 | Farag et al. | |
| 2009/0059028 A1 * | 3/2009 | Kollias | A61B 5/0071 348/222.1 |
| 2009/0082642 A1 * | 3/2009 | Fine | A61B 5/0059 600/300 |
| 2009/0247853 A1 | 10/2009 | Debreczeny | |
| 2009/0306484 A1 * | 12/2009 | Kurtz et al. | 600/300 |
| 2009/0306487 A1 * | 12/2009 | Crowe | A61B 5/02433 600/322 |
| 2011/0251493 A1 * | 10/2011 | Poh et al. | 600/477 |

FOREIGN PATENT DOCUMENTS

| | | |
|---|---|---|
| CN | 101502414 A | 8/2009 |
| EP | 1764034 A2 | 3/2007 |
| EP | 2087837 A1 | 8/2009 |
| JP | 11197126 A | 7/1999 |
| JP | 2005095193 A | 4/2005 |
| WO | 1997015229 A1 | 5/1997 |
| WO | WO 9932030 A1 * | 7/1999 |
| WO | 0044274 A2 | 8/2000 |
| WO | WO0062661 A1 | 10/2000 |
| WO | WO02074162 A1 | 9/2002 |
| WO | 2005051190 A1 | 6/2005 |
| WO | WO2009092162 A1 | 7/2009 |

OTHER PUBLICATIONS

Verkruysse et al: "Remote Plethysmographic Imaging Using Ambient Light"; Optics Express, vol. 16, No. 26, Dec. 2008, pp. 21434-21445.

Viola et al: "Robust Real-Time Object Detection"; Proceedings of IEEE Second International Workshop on Statistical and Computational Theories of Vision-Modeling, Learning, Computing, and Sampling, Vancouver, Canada, Jul. 2001, 25 Page Article.

De Haan et al: "True-Motion Estimation With 3-D Recursive Search Block Matching"; IEEE Transactions on Circuits and Systems for Video Technology, vol. 3, No. 5, Oct. 1993, No. 368-379.

Verkruysse, W. et al., "Remote Plethysmographic Imaging using Ambient Light", Optics Express, vol. 16, No. 26, pp. 1-16, Dec. 2008.

* cited by examiner

METHOD AND SYSTEM FOR CARRYING OUT PHOTOPLETHYSMOGRAPHY

FIELD OF THE INVENTION

The invention relates to a method of photoplethysmography, a system for carrying out photoplethysmography, and a computer program.

FIELD OF THE INVENTION

Verkruysse, W. et al., "Remote plethysmographic imaging using ambient light", *Optics Express* 16 (26), 22 Dec. 2006, pp. 21434-21445 discloses a method in which photoplethysmographic signals were measured remotely using ambient light and a simple consumer-level digital camera in movie mode. Heart and respiration rates could be quantified up to several harmonics. Although the green channel featured the strongest photoplethysmographic signal, corresponding to an absorption peak by (oxy-)hemoglobin, the red and blue channels also contained photoplethysmographic information.

A problem of the known method is that the green channel may be subject to noise that makes it difficult to retrieve the photoplethysmographic signal of interest. This is true to an even greater extent of the other channels, which are only weakly correlated with the biometric signal.

SUMMARY OF THE INVENTION

It is desirable to provide a method and system of the types mentioned above that increase the likelihood of being able to retrieve a relatively clear biometric signal even where there is noise in the green channel.

This object is achieved by the method according to the invention, which includes:

processing a signal based on at least one signal from at least one sensor arranged to capture light from a living subject to extract information on a characteristic of a periodic biological phenomenon, wherein at least one of the signals from at least one sensor is obtained by using at least one of a light source and a filter placed before the at least one sensor tuned to a peak in an absorption spectrum of water.

Thus, the method makes use of a channel sensitive to variations in reflected and/or transmitted light due to pulsating blood plasma flow. The signal in this channel can be used in addition to or as an alternative to a channel sensitive to variations in the amount of oxyhemoglobin in the illuminated area. Because a different frequency of light is used, there is a greater likelihood that a stronger signal will be obtained in circumstances in which there is noise in a green channel.

In an embodiment, the peak is in a range corresponding to a range of wavelengths of electromagnetic radiation in air of above 750 nm.

This embodiment is suitable for use in situations in which it is undesirable to have visible light. Examples include public spaces, military triage, monitoring at night and neonatal incubators.

In a variant of this embodiment, the peak is in a range corresponding to a range of wavelengths smaller than 1100 nm.

This embodiment has the effect that it is possible to use photosensors (including arrays of photodiodes) implemented in silicon technology. Such sensors generally show a peak in their sensitivity around 800 nm or 900 nm. At 1000 nm, the sensitivity is slightly lower, but still high enough to detect photons in this spectral range, in which there are also favorable peaks in the absorption spectrum of water, in particular at 970 nm. There are many commercially available and cheap silicon-based sensors, e.g. CMOS and CCD arrays.

An embodiment of the method includes directing polarized light onto the living subject and capturing light from the living subject through a polarization dependent filter.

This embodiment has the effect of eliminating ambient light, including in particular also light with periodic components.

In an embodiment, the signal obtained by using at least one of a light source and a filter placed before the at least one sensor tuned to a peak in the absorption spectrum of water is obtained from a first sensor and a second signal is obtained from a second sensor, arranged to capture light from the living subject in a different wavelength range than the first sensor.

The signal from the first sensor, although including a strong component representative of pulsating blood flow, can also include artefacts due to movement of the living subject and/or illumination changes. The second signal can be representative of captured light in a wavelength range that is not particularly sensitive to blood flow changes, but that includes the same artefacts due to movement of the living subject and/or illumination changes. Thus, the second signal can be used to correct the first signal by removing components not representative of generally periodic biological phenomena.

A variant of this embodiment includes using a beam splitting arrangement to split light from the living subject into a beam directed onto the first sensor and a beam directed onto the second sensor.

This makes the correction carried out using the signal from the second sensor more accurate, because the signals both include components representative of illumination changes or movements of the same surface area of the living subject. The splitting can be in the wavelength domain or it can be a polarization split.

A further variant includes subtracting a signal at least based on only the second of the first and second signals from a signal at least based on only the first of the first and second signals.

This variant can be implemented using relatively simple signal processing techniques. Complicated signal analysis is not required. The subtraction can in particular also be carried out in the time domain. The signals used in the subtraction operation can be at least based on the signals from the first and second sensors in that they correspond or in that they are obtainable by applying a gain smaller or larger than one, depending on the implementation.

A further variant includes, prior to using the sensors to capture light from the living subject, using the sensors to capture light from a calibration surface and adjusting parameters affecting at least one of the capture of light and a provision of signals at least based on the signals from the sensors, so as to adjust at least one of amplitude and phase of the respective signals at least based on the signals from the first and second sensors to each other.

An effect is that the signals from the first and second sensors, or signals based on these respective signals by being obtainable by simple multiplication, for instance, can be directly subtracted from one another, in particular also in the time domain, when the method is applied to the living subject.

According to another aspect of the invention, there is provided a system for carrying out photoplethysmography, including:

at least one sensor for capturing light from a living subject;

a signal processing system arranged to process a signal based on at least one signal from the at least one sensor to extract information on a characteristic of a periodic biological phenomenon; and at least one of a light source and a filter placed before at least one of the sensors tuned to a peak in an absorption spectrum of water.

In an embodiment, the system is arranged to carry out a method according to the invention.

BRIEF DESCRIPTION OF THE DRAWINGS

The invention will be explained in further detail with reference to the accompanying drawings, in which.

DETAILED DESCRIPTION OF THE EMBODIMENTS

Several embodiments of a system for remote photoplethysmography will be explained herein. Photoplethysmography is a method for characterizing certain periodic physiological phenomena using skin reflectance variations. The human skin can be modeled as an object with at least two layers, one of those being the epidermis (a thin surface layer) and the other the dermis (a thicker layer underneath the epidermis). Approximately 5% of an incoming ray of light is reflected in the epidermis, which is the case for all wavelengths and skin colors. The remaining light is scattered and absorbed within the two skin layers in a phenomenon known as body reflectance (described in the Dichromatic Reflection Model). The epidermis behaves like an optical filter, mainly absorbing light. In the dermis, light is both scattered and absorbed. The absorption is dependent on the blood composition, so that the absorption is sensitive to blood flow variations. The optical properties of the dermis are generally the same for all human races. The dermis contains a dense network of blood vessels, about 10% of an adult's total vessel network. These vessels contract according to the blood flow in the body. They consequently change the structures of the dermis, which influences the reflectance of the skin layers. Consequently, the heart rate can be determined from skin reflectance variations.

A first system for photoplethysmography (FIG. 1) comprises a light source 1 and an optical system for focusing light from the light source onto an area of exposed skin of a living subject, e.g. a human being. The optical system in the illustrated embodiment comprises a beam splitter 2 and a first lens 3.

Figure 1:
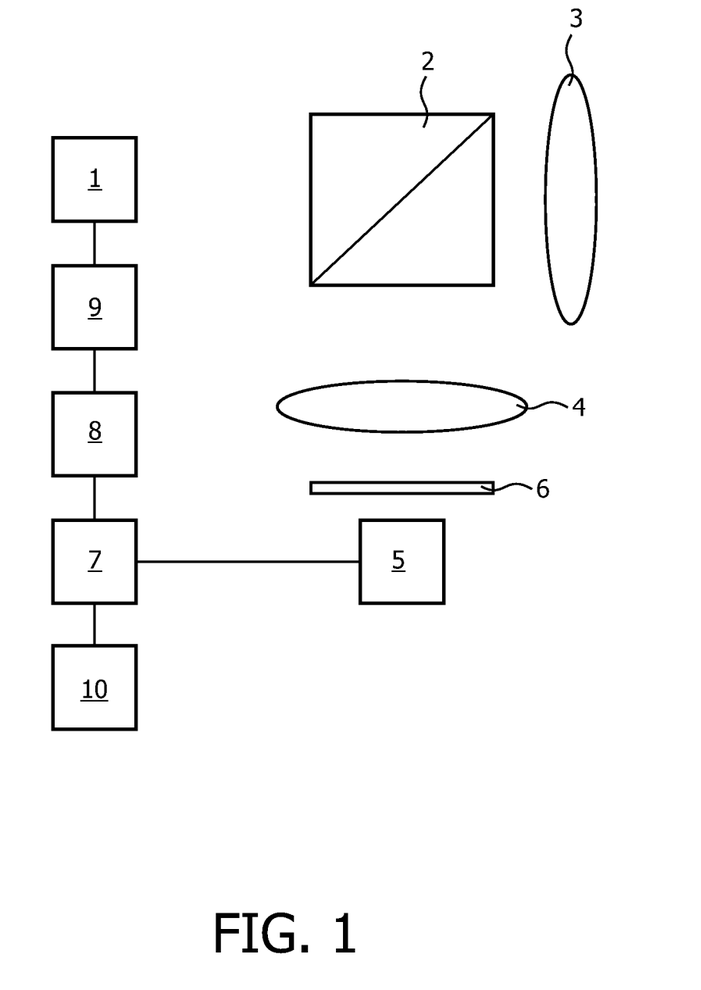
FIG. 1 is a schematic diagram of a first system for remote photoplethysmography.

Reflected light is collected by the first lens 3, reflected in the beam splitter 2 and focused by a second lens 4 onto a photosensor 5. In other embodiments, the optical system comprises further elements, including one or more elements such as lenses, concentrators, beam splitters, prisms and the like.

In the illustrated embodiment, the light passes a filter 6. The filter 6 is at least wavelength-dependent, being arranged to pass a narrow band of wavelengths centered on a wavelength corresponding to a peak in the absorption spectrum of water. The pass-band has a width dependent on the position of the peak in the absorption spectrum of water. Generally, the width is such that the full width half maximum of the absorption peak is contained within the pass-band. The width can therefore range from 100 nm to 1·m. Peaks in the absorption spectrum of water occur at frequencies corresponding to wavelengths of 514, 606, 660 and 739 nm within the visible spectrum. Further peaks occur at 836 and 970 nm just outside the visible part of the spectrum. The latter values are used in embodiments in which ambient lighting levels are low and the light source 1 should not emit too much visible light. Indeed, in certain such embodiments, the light source 1 is not used at all, the signal provided by the photosensor 5 being entirely due to reflected ambient electromagnetic radiation.

In embodiments in which the light source 1 is used, the filter 6 and the light source 1 can be polarization-dependent. In this way, the signal from the photosensor 5 can be kept generally free of variations due to changing ambient light levels.

In the illustrated embodiment, the signal from the photosensor 5 is obtained by a data processing device 7, which can be a programmed general-purpose computing device or an application-specific device.

The data processing device 7 also provides control signals to a controller 8 and driver 9 for powering the light source 1. In an embodiment, these two components 8, 9 are integrated into a single device with the data processing device 7.

In order to increase the signal-to-noise ratio of the signal from the photosensor 5, heterodyne detection can be employed. The light emitted by the light source 1 is modulated at a certain frequency v. The photosensor 5 will therefore provide a signal that is at the same frequency and light at other frequencies. The light at the other frequencies can be rejected.

In an embodiment, the light source 1 is arranged to emit light with a broad spectrum. In another embodiment, the light source 1 is tuned to a frequency corresponding to a peak in the absorption spectrum of water. In particular, this frequency is generally the same as the one to which the wavelength-dependent filter 6 is tuned. If the frequency corresponds to a wavelength in air of 836 nm or 970 nm, then no visible electromagnetic radiation is emitted.

The data processing device 7 carries out such operations as filtering and analysis. In particular, the data processing device 7 is arranged to determine the frequency at which the spectrum of the signal or filtered signal has a local maximum, at least in a pre-determined range corresponding to the range in which a signal associated with a periodic biological phenomenon is expected to be present. Thus, the heart rate or respiration rate of the individual from whom the captured light emanates can be determined. Information representative of the determined value is provided on an output device 10.

Figure 2:
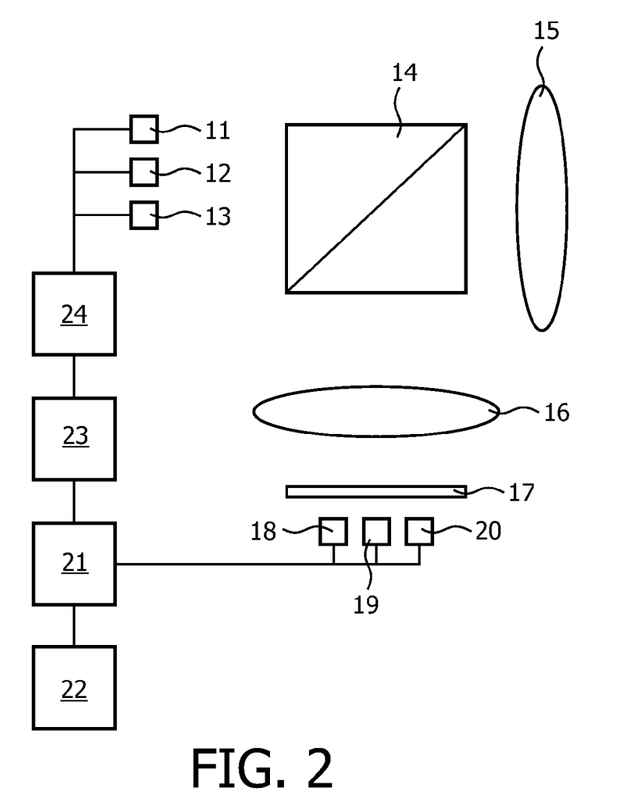
FIG. 2 is a schematic diagram of a second system for remote photoplethysmography.

It is also possible to use light at a frequency corresponding to a peak in the absorption spectrum of water in addition to light at a different frequency. This is illustrated in FIG. 2, where a system similar to the system of FIG. 1, but with three light sources 11-13, is shown. In the illustrated embodiment, use is also made of an optical system comprising a beam splitter 14, a first lens 15 for focusing light onto exposed skin of a living being and collecting light reflected back from the skin, and a second lens 16 and polarization-dependent filter 17.

Each of the three photosensors 18-20 is sensitive to electromagnetic radiation in a different range of the spectrum, at least one of these ranges being limited. The three ranges may overlap.

One of the three photosensors 18-20 is tuned to a peak in the absorption spectrum of water. In one example, another of the three photosensors 18-20 is tuned to a range of wavelengths within the range from 500 nm to 600 nm, corresponding to green light. This sensor is thus sensitive to variations in the amount of oxyhemoglobin in the skin. The third of the three sensors 18-20 can be tuned to a range of wavelengths that is not especially sensitive to variations in the reflectance of the skin. Indeed, the third of the photosensors 18-20 can simply detect changes in light intensity across the entire spectrum.

The signals from the photosensors 18-20 are provided to a data processing device 21 that processes them to provide a signal that can be analyzed to determine a characteristic of a component corresponding to a periodic biological phenomenon, e.g. a heart rate value. To this end, correlations between the signal from the sensor tuned to green light and the signal from the sensor tuned to a peak in the absorption spectrum of water can be determined, whereas the signals can be decorrelated from the signal from the third sensor. This yields a single signal that has a relatively clean and strong component due to skin reflectance changes. Analysis of the signal is carried out by the data processing device 21 in order to determine a characteristic of the signal, e.g. the frequency (step 47). Information representative of the characteristic is provided on an output device 22.

For further improvement of the signal-to-noise ratio, the illustrated embodiment makes use of tuned light sources 11-13 arranged to emit light within ranges of the electromagnetic radiation spectrum corresponding to those to which the photosensors 18-20 are tuned. A driver 23 and controller 24 are provided to power the light sources 11-13. The controller 24 is connected to the data processing device 21.

As in the embodiment of FIG. 2, heterodyne detection can be used to improve the signal-to-noise ratio still further.

Figure 3:
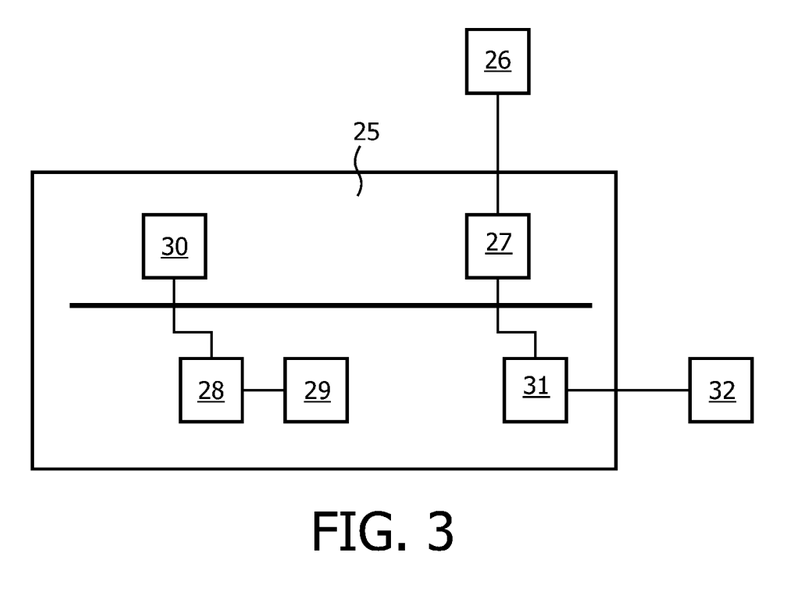
FIG. 3 is a schematic diagram of third system for remote photoplethysmography.

Turning to FIG. 3, a system for remote photoplethysmography using imaging comprises a data processing system 25 and a video camera 26. The video camera 26 is arranged to provide a sequence of images to an interface 27 of the data processing system 25. The data processing system 25 includes a data processing device 28 and main memory 29 for executing instructions included in software stored on a mass-storage device 30. The data processing system 25 further comprises an interface to an output device 32 such as a display.

Figure 4:
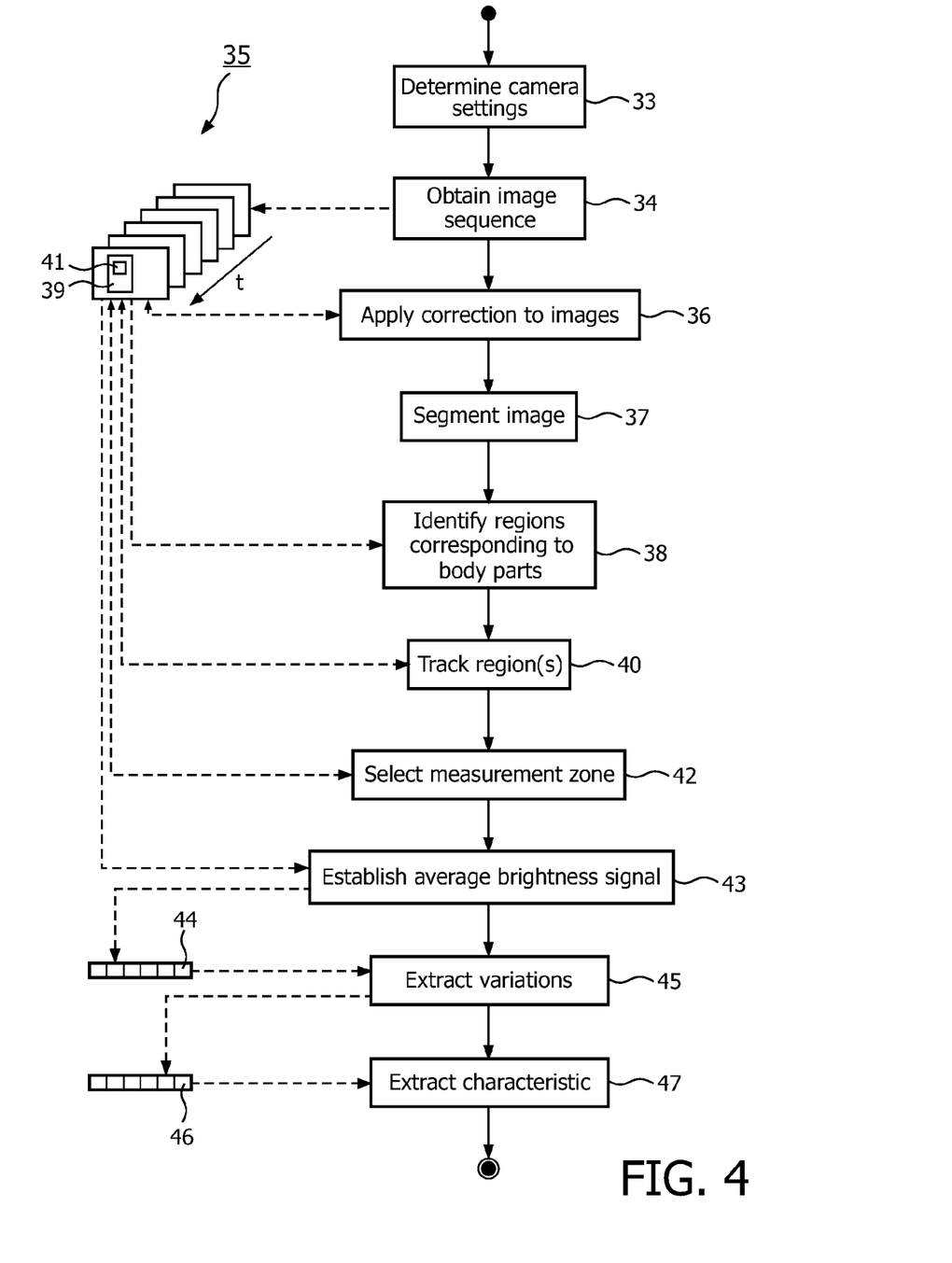
FIG. 4 is a flow chart illustrating steps in a first method of obtaining a signal for analysis to determine a characteristic of a periodic biological phenomenon.

A first embodiment of a photoplethysmographic method carried out by the data processing system 25 is illustrated in FIG. 4.

In this embodiment, an initialization step 33 is completed first, in order to determine appropriate settings for the video camera 26. To this end, the data processing system 25 causes at least one of the frame rate, exposure time, pixel clock (the setting determining the rate at which pixel values are acquired) and gain of the camera channel of the video camera 26 to be varied whilst a sequence of digital images is captured. The (spatial) average brightness of at least part of each image of the sequence is determined, and the magnitude of periodic fluctuations in the average brightness is determined for each new value of the settings. Those settings for which the magnitude within at least a range of the spectrum, in particular a range up to 100 Hz, is smallest are selected for subsequent use in the method. Instead of determining the spatial average brightness of at least a part of the image, an individual pixel's brightness fluctuations can be determined. The effect of choosing the settings of the video camera 26 is that periodic background lighting fluctuations are absent to the largest extent possible from sequences of images to which the remainder of the method is applied.

In a next step 34, a sequence 35 of images is obtained from the video camera 26.

In one embodiment, the video camera 26 is provided with a single filter tuned to a wavelength corresponding to a peak in the absorption spectrum of water. In particular, as in the embodiments discussed above, this can be a wavelength corresponding to a frequency in the visible part of the spectrum, e.g. 514, 606, 660 or 739 nm. In another embodiment, the frequency can be just outside the visible range of the spectrum, e.g. 836 nm or 970 nm, which again allows for the use of common silicon-based photosensor arrays that are sensitive in that part of the spectrum.

In an alternative embodiments, the video camera 26 is provided with a plurality of filters, so that each image in the sequence 35 corresponds to a plurality of image frames, each comprising an array of pixel values representative of light intensity in a different range of the spectrum of electromagnetic radiation. At least one sequence of image frames corresponds to a limited range centered on a frequency corresponding to a peak in the absorption spectrum of water.

Subsequently, the images 35 are processed (step 36) to remove non-periodic background signals. To this end, a correction signal corresponding to a time-varying average brightness of part or all of the images 35 is formed. In the illustrated embodiment, the pixel data of the images 35 are then decorrelated from the correction signal. Algorithms for cancelling non-linear cross-correlations are known per se. Further image processing may take place at this stage 36, e.g. to compensate for camera motion.

In two next steps 37, 38, an image segmentation method is performed on at least one of the sequence 35 of images. In particular, an algorithm for detecting a body part, generally the face of a human being, is carried out in these steps 37, 38. A suitable algorithm is described in Viola, P. and Jones, M. J., "Robust real-time object detection", *Proc. Of IEEE Workshop on statistical and computational theories of vision*, 13 Jul. 2001. Other suitable algorithms based on recognizing segments with certain shapes and/or colors (skin colors, for example) are known and can be used instead of or in addition to this algorithm described in the literature.

At least one distinct segment 39 determined to correspond to a body part of the desired type is tracked (step 40) through the sequence 35 of images. That is to say that the segment 39 is placed, i.e. its location determined, by comparing the images in the sequence 35 to quantify movement of the body part within the images 35. A suitable tracking algorithm is known, for example, from De Haan et al., "True-motion estimation with 3-D recursive search block matching", *IEEE Transactions on circuits and systems for video technology*, 3 (5), October 1993, pp. 368-379.

Subsequently, for each selected and tracked segment 39, a measurement zone 41 within the image segment 39 is selected (step 42). This step 42 involves a spatial analysis of the pixel data of a plurality of image parts—each part being one or more image points in size—to determine a set of contiguous parts having similar characteristics. These parts are selected to form the measurement zone 41. The position of the measurement zone 41 is determined relative to the tracked segment 39 in which it is comprised, so that it is likewise tracked.

A next step 43 involves the generation of a brightness signal 44 of which each value is a combination of pixel values from the measurement zone 41 in a particular one of the sequence 35 of images.

Where the images comprise image frames corresponding to different ranges in the electromagnetic radiation spectrum, this step 43 can include a plurality of steps (not shown in detail), in which a separate signal is formed for each sequence of image frames. These separate signals are then processed to provide a single signal 44. In particular, where one sequence of image frames corresponds to a frequency range corresponding to a peak in the absorption spectrum of water and another sequence corresponds to green light, only the common signal components can be kept. A sequence corresponding to a general intensity level or a sub-range not sensitive to variations due to pulsating blood flow can be used to remove noise.

Then (step 45), the brightness signal 44 is centered on its mean value, yielding a final signal 46 representative of at least variations in a value based on a plurality of pixel values from each of the sequence 35 of images. In alternative embodiments, a different technique for extracting variations of the order of 1% of the dynamic range of the brightness signal 44 is used, e.g. a filtering operation involving a differentiation step.

Finally (step 47) a characteristic of the periodic biological phenomenon being monitored is extracted. This can be the heart rate of an individual being monitored, for instance. Using, for example, a Fast Fourier Transform, a local maximum in the spectrum of the signal 46 can be determined.

Figure 5:
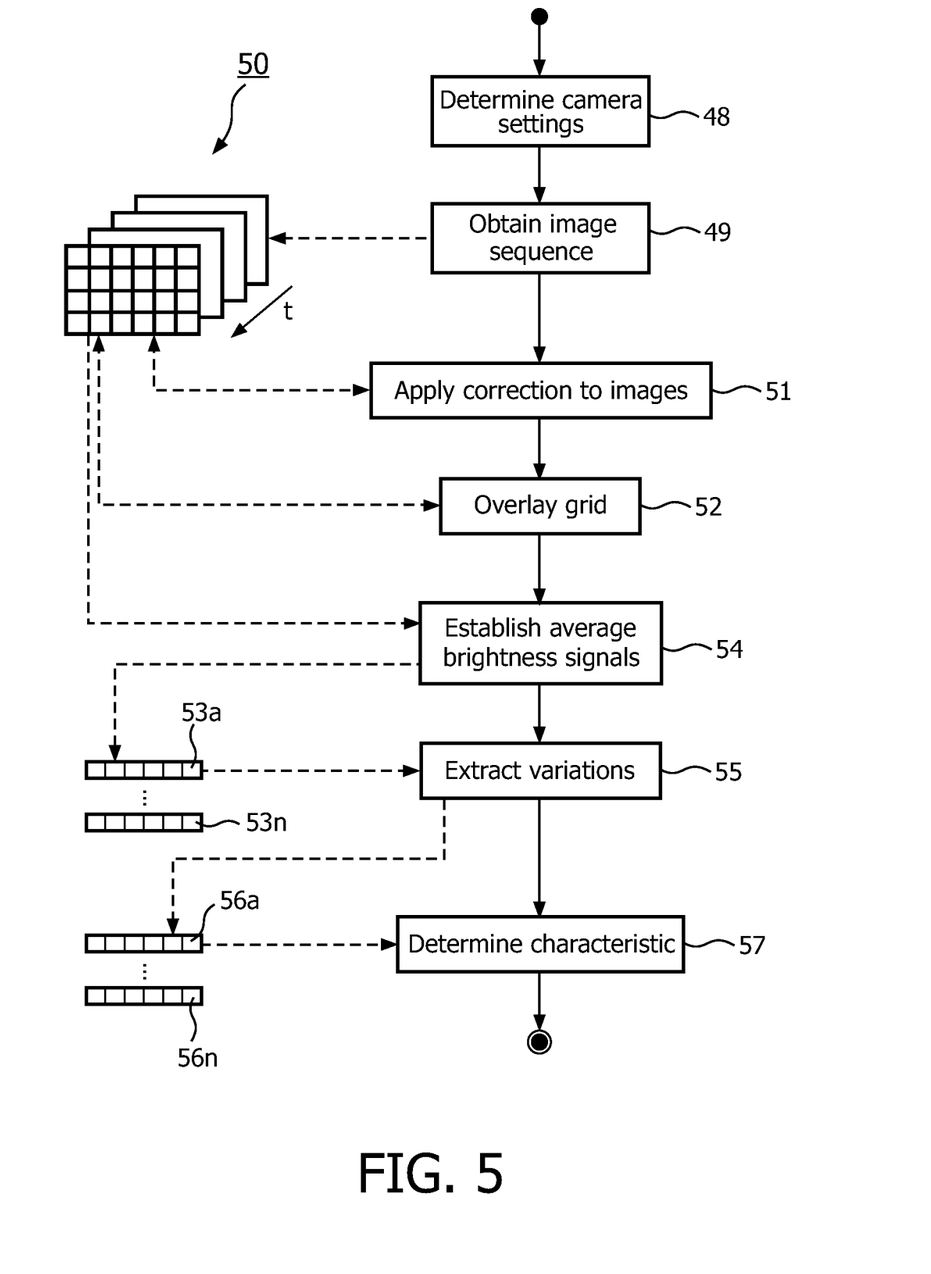
FIG. 5 is a flow chart illustrating steps in a second method of obtaining a signal for analysis to determine a characteristic of a periodic biological phenomenon.

An alternative method to that of FIG. 4 is illustrated in FIG. 5. This embodiment also allows one to generate phase maps, for example.

The method of FIG. 5 also commences with an initialization step 48 for determining appropriate settings for the video camera 26. The data processing system 25 causes at least one of the frame rate, exposure time, pixel clock (the setting determining the rate at which pixel values are acquired) and gain of the camera channel of the video camera 26 to be varied whilst a sequence of digital images is captured. The (spatial) average brightness of at least part of each image of the sequence is determined, and the magnitude of periodic fluctuations in the average brightness is determined for each new value of the settings. Those settings for which the magnitude within at least a range of the spectrum, in particular a range up to 100 Hz, is smallest are selected for subsequent use in the method. Instead of determining the spatial average brightness of at least a part of the image, an individual pixel's brightness fluctuations can be determined.

Then (step 49), an image sequence 50 is obtained. As in the embodiment of FIG. 4, this sequence 50 can be comprised of a plurality of sequences of image frames, each corresponding to a different part of the spectrum of electromagnetic radiation (i.e. a different color channel if only the visible spectrum is used).

The images 50 are processed to remove non-periodic background signals using a correction signal corresponding to a time-varying average brightness of part or all of the images 50 (step 51). This step is similar to the corresponding step 36 in the method of FIG. 4.

Then (step 52), a grid is laid over the images 50, which grid partitions each image into a plurality of measurement zones, or at least potential measurement zones. Each measurement zone includes a plurality of pixel values.

Signals 53a-n are extracted (step 54) for at least one, but more generally a plurality of measurement zones as defined by the grid. This step 54 involves combining pixel values from a measurement zone into a single value, such that each value of the signal 53 is based on pixel values from only one of the images 50. The result is thus a set of time-varying signals 53a-n representative of the brightness of an associated measurement zone. In one embodiment, pixel values are combined by averaging. In another embodiment, pixel values are combined by taking the mean value. The combination removes random noise, leading to a signal with a stronger component corresponding to a periodic biological phenomenon.

Where the sequence 50 of images is comprised of a plurality of sequences of image frames, each associated with a different range of the spectrum of electromagnetic radiation, pixel values from corresponding measurement zones in each of the image frames making up an image are combined. The combination is such as to remove background signals or enhance components corresponding to biological signals. Thus, where the image frames comprise pixel values corresponding to intensity values in a range of the spectrum centered on a peak in the absorption spectrum of water and pixel values corresponding to intensity values in a range of the spectrum within the range between 500 nm and 600 nm, the combination step 54 can include a cross-correlation step.

Next (step 55), the signals 53a-n are centered on their means, yielding a further set of signals 56a-n representative of at least variations in a value based on pixel values of associated respective measurement zones. Instead of centering the signals 53a-n on their mean, another operation suitable for extracting variations of the order of 1% of the dynamic range of the signals 53a-n can be applied, e.g. differentiation or a similar filtering operation.

Finally (step 57), a characteristic of at least a component of at least one of the final signals 56a-n is determined. For example, the frequency of a local maximum in the spectrum of the signals 56a-n can be determined, in order to establish a value of the heart rate of a person represented in the sequence 50 of images. In another embodiment, in which all the measurement zones are used, a phase map is created. In another embodiment, clustering of signals 56a-n or values obtained from the final signals 56a-n is used to establish a consensus value characterizing a biological phenomenon.

Figure 6:
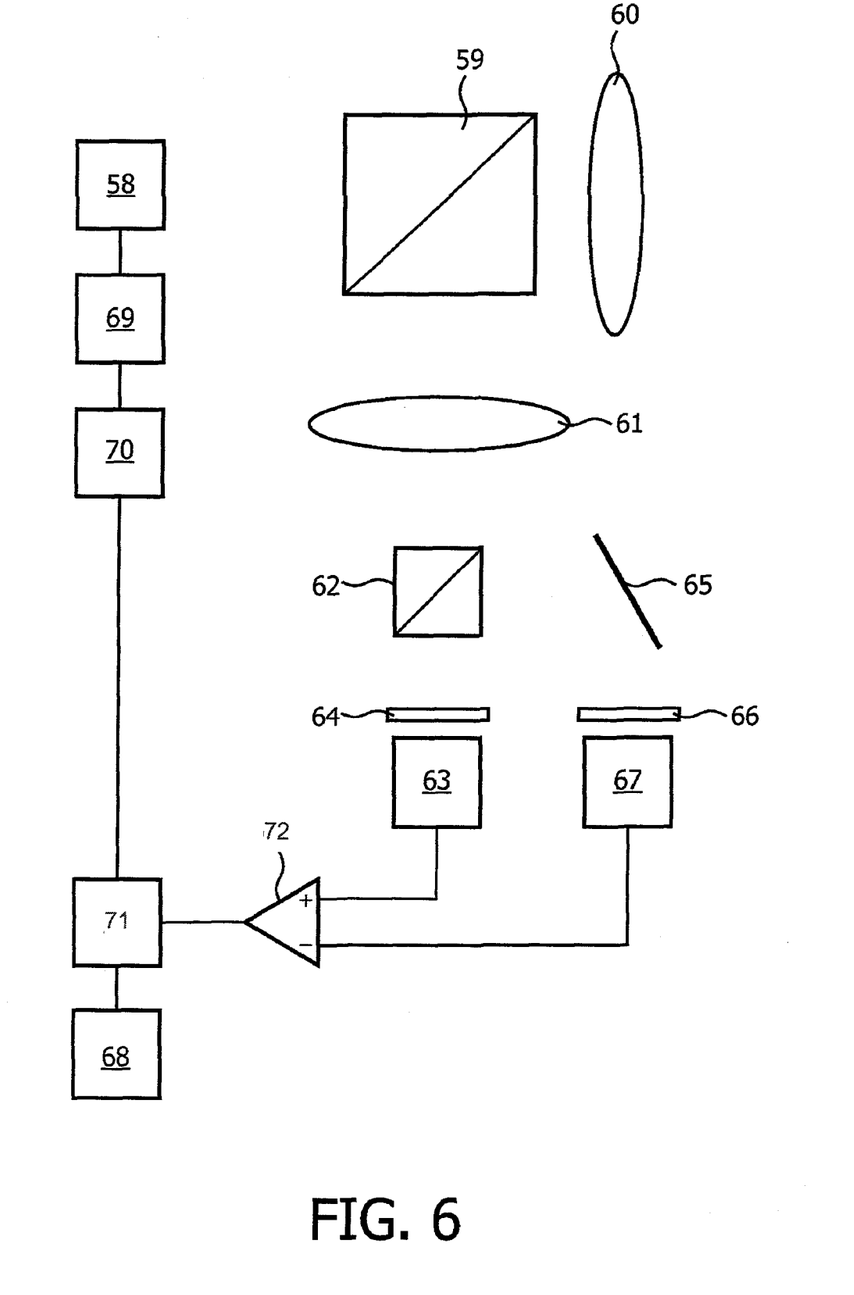
FIG. 6 is a schematic diagram of a fourth system for remote photoplethysmography.

A quite different embodiment of a system for photoplethysmography is illustrated in FIG. 6. This system obtains two signals, one of which is used to remove motion and illumination artefacts from the other.

In the illustrated embodiment, the system includes a light source 58. The light source 58 can emit a spectrum with two peaks, it can emit a continuum spectrum or it can emit light with both characteristics. In an alternative embodiment, the light source 58 is not used. Ambient (white) light is used instead.

The system of FIG. 6 also includes an optical system comprising a first beam splitter 59, a first lens 60 for focusing light from the light source 58 onto exposed skin of a living being and collecting light reflected back from the skin, and a second lens 61.

Light collected by the second lens 61 is passed on to a second beam splitter 62. The second beam splitter 62 can be a polarization-dependent or wavelength-dependent beam splitter. It splits light comprising at least two wavelengths into separate beams.

A first beam is directed onto a first sensor 63 via a first filter 64. The first filter 64 is tuned to a peak in the absorption spectrum of water. In an embodiment, the peak is in a range corresponding to a range of wavelengths above 750 nm. In addition, the range may end below 1100 nm.

A second beam is directed via a mirror 65 and a second filter 66 onto a second sensor 67. The second filter 66 is arranged to pass light in a different wavelength range than the first filter 64, so that the second sensor 67 is arranged to capture light from the living subject in a different wavelength range than the first sensor 63.

It is observed that the different wavelength range can overlap the wavelength to which the first filter 64 is tuned. In particular, the second filter 66 can be omitted altogether, so that the second sensor 67 provides a signal representative of ambient light levels.

In general, however, the different wavelength range will be disjoint from the pass-band of the first filter 64.

The signals from the sensors 63, 67 are provided to a signal subtraction device 68 (e.g. an operational amplifier), so that the signal from the second sensor 67 is subtracted from that from the first sensor 63.

The result is provided to a data processing device 71 that processes, e.g. analyses, the difference signal to provide an output characteristic of a component corresponding to a periodic biological phenomenon, e.g. a heart rate value. Analysis of the signal by the data processing device 21 can include the determination of a characteristic of the signal, e.g. the frequency. Information representative of the characteristic is provided on an output device 68.

For further improvement of the signal-to-noise ratio, heterodyne detection can be used, to which end a driver 69 and controller 70 are provided to power the light source 58.

In order to ensure that the signal subtracted from the signal from the first sensor 63 indeed removes components due to motion of the living subject and/or illumination changes in the environment of the living subject, a calibration step is carried out prior to use of the system of FIG. 6 on a living subject.

In the calibration step, a calibration surface is provided, onto which light from the light source 58 is focused. This calibration surface is, in one embodiment, a white diffuser with known scattering properties (such as wavelength, angle to an optical axis of the first lens 60 and polarization). Then, the sensitivity and gain of the two sensors 63, 67 are adjusted in such a way that the signals provided to the signal subtraction device 72 are identical in phase and amplitude. In one embodiment, this calibration phase is carried out for different combinations of angles, wavelengths and polarizations. The calibration need not be carried out in the field, but can be carried out when the system of FIG. 6 is manufactured. In an embodiment, the data processing device 71 is used to recall the correct settings.

It should be noted that the above-mentioned embodiments illustrate, rather than limit, the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The mere fact that certain measures are recited in mutually different dependent claims does not indicate that a combination of these measures cannot be used to advantage.

In a variant of the embodiments of FIGS. 1-3, the data processing device 7, 21 or data processing system 25 provides an output signal having a frequency corresponding to that of the periodic biological phenomenon of interest, which can be used to gate a further device (not shown), such as an imaging device.

In a variant of the embodiment of FIG. 3, the data processing system 25 includes an interface to one or more light sources. One of the light sources can be tuned to a peak in the absorption spectrum of water, in particular one of the wavelength values in the near-infrared part of the electromagnetic spectrum given above.

The invention claimed is:

1. A method of remote photoplethysmography, as to a living subject comprising:
   directing polarized light from at least one light source onto an area of exposed skin of the living subject;
   generating a plurality of signals corresponding to light reflected from the living subject captured by a respective at least one of a plurality of sensors sensitive to electromagnetic radiation in a respective one of different ranges of a spectrum including
      a first range having a peak in an absorption spectrum of water, the first range being a subset of the spectrum,
      a second range corresponding to green light for sensing variations in an amount of oxyhemoglobin in a skin of the living subject, the second range being a subset of the spectrum, and
      a third range for sensing changes in light intensity across the entire spectrum;
   generating an analysis signal corresponding to a periodic biological phenomenon by decorrelating signals of the plurality of signals produced from light captured in the third range from the plurality of signals; and
   analyzing the analysis signal to determine at least one characteristic relating to a biological phenomenon of the living subject.

2. The method according to claim 1, wherein the peak is in a range corresponding to a range of wavelengths of electromagnetic radiation in air of above 750 nm.

3. The method according to claim 2, wherein the peak is in a range corresponding to a range of wavelengths of electromagnetic radiation in air smaller than 1100 nm.

4. The method according to claim 1, further comprising: directing polarized light to the living subject, and wherein the captured light is filtered via a polarization dependent filter.

5. The method according to claim 1, wherein the second range is 500 nm to 600 nm.

6. The method according to claim 1, further comprising: using a beam splitting arrangement to split light reflected from the living subject into a plurality of beams directed onto the plurality of sensors sensitive to electromagnetic radiation in the first and second ranges.

7. The method according to claim 6, wherein
   splitting using a beam splitting arrangement is performed in at least one of the wavelength domain or in the polarization domain.

8. The method according to claim 7, further comprising: directing polarized light to the living subject, wherein the generating includes filtering light reflected by the living subject via a polarization dependent filter.

9. The method according to claim 1, further comprising: subtracting the signal in the second range from the signal in the first range.

10. The method according to claim 9, further comprising, prior to capturing light reflected by the living subject, capturing light from a calibration surface and adjusting parameters affecting at least one of the capture of light and a provision of at least one of the signals in the first and second ranges.

11. The method according to claim 1, wherein a sensor of the plurality of sensors that senses radiation in the third range detects changes in light intensity.

12. The method according to claim 1, wherein the peak in absorption spectrum of water is one of the group consisting of: 514 nm, 606 nm, 660 nm, 739 nm, 836 nm, or 970 nm.

13. The system according to claim 1, wherein the entire spectrum is greater than the combination of the first range and the second range.

14. A system for carrying out photoplethysmography as to a living subject, comprising:
- at least one light source for directing polarized light onto an area of exposed skin of the living subject;
- at least one filter for filtering light reflected from the living subject;
- a plurality of sensors sensitive to electromagnetic radiation in different ranges of the spectrum including at least a respective sensor for each of:
  - a first range having a peak in an absorption spectrum of water,
  - a second range corresponding to green light for sensing variations in an amount of oxyhemoglobin in the skin, and
  - a third range for sensing changes in light intensity across the entire spectrum,
- wherein, each of the plurality of sensors is configured to capture light reflected by the living subject and produce a plurality of signals corresponding to the captured light; and
- a processing system configured to extract a signal of a periodic biological phenomenon by decorrelating signals of the plurality of signals produced from light captured in the third range from the plurality of signals.

15. A system for carrying out photoplethysmography as to a living subject, comprising:
- a plurality of sensors configured to capture light sensitive to electromagnetic radiation that is reflected by a living subject, and to produce a plurality of corresponding signals, the light is captured in at least three ranges of the spectrum including:
  - a first range having a peak in an absorption spectrum of water,
  - a second range corresponding to green light for sensing variations in an amount of oxyhemoglobin in a skin of the living subject, wherein at least one of the plurality of sensors tuned to the second range is sensitive to variations in an amount of oxyhemoglobin in the skin, and
  - a third range including an entire spectrum for sensing changes in light intensity across the entire spectrum,
  - wherein light in each of the ranges is captured by at least one respective corresponding sensor of the plurality of sensors; and
- a processing system configured to extract a signal of a periodic biological phenomenon by decorrelating signals of the plurality of signals produced from light captured in the third range from the plurality of signals.

16. The system of claim 15, wherein the peak is in a range corresponding to a range of wavelengths of electromagnetic radiation in air of above 750 nm.

17. The system of claim 16, wherein the peak is in a range corresponding to a range of wavelengths of electromagnetic radiation in air smaller than 1100 nm.

18. A system for carrying out photoplethysmography as to a living subject, comprising:
- at least three sensors configured to capture light sensitive to electromagnetic radiation that is reflected by a living subject, and to produce a plurality of corresponding signals, wherein
  - a first of the at least three sensors captures light in a range of the spectrum having a peak in an absorption spectrum of water,
  - a second of the at least three sensors captures light in a range corresponding to green light, senses variations in an amount of oxyhemoglobin in the skin, and
  - a third of the at least three sensors captures light in a range including an entire spectrum for sensing changes in light intensity across the entire spectrum, and is less sensitive to variations in the reflectance of the skin than other sensors of the at least three sensors; and
- a processing system configured to extract information characteristic of a periodic biological phenomenon by decorrelating signals of the plurality of signals produced from light captured in the third range from the plurality of signals.

19. The system of claim 18, wherein the peak is in a range corresponding to a range of wavelengths of electromagnetic radiation in air of above 750 nm.

20. The system of claim 19, wherein the peak is in a range corresponding to a range of wavelengths of electromagnetic radiation in air smaller than 1100 nm.

* * * * *